United States Patent [19]

Arichi et al.

[11] 4,317,816

[45] Mar. 2, 1982

[54] SAPONIN CONTAINING COMPOSITION EFFECTIVE AGAINST ADRENAL ATROPHY

[75] Inventors: Shigeru Arichi; Yoshihiro Uchida, both of Osaka, Japan

[73] Assignee: Osaka Chemical Laboratory Co., Ltd., Osaka, Japan

[21] Appl. No.: 172,006

[22] Filed: Jul. 24, 1980

[30] Foreign Application Priority Data

Aug. 13, 1979 [JP] Japan ............................ 54-103336

[51] Int. Cl.³ .................. A61K 31/705; A01N 31/00; A61K 31/56
[52] U.S. Cl. ...................................... 424/182; 424/240
[58] Field of Search ................... 424/182, 240, 238

[56] References Cited

U.S. PATENT DOCUMENTS 3,284,304 11/1966 Montandraud .................... 424/182
4,157,894 6/1979 Bombardelli ....................... 424/182

*Primary Examiner*—Elbert L. Roberts
*Attorney, Agent, or Firm*—Hubbell, Cohen, Stiefel & Gross

[57] ABSTRACT

This invention is directed to a pharmaceutical composition containing saponin and a method of using the saponin containing composition for preventing and treating adrenal atrophy and other organ diseases.

26 Claims, No Drawings

4,317,816

SAPONIN CONTAINING COMPOSITION EFFECTIVE AGAINST ADRENAL ATROPHY

BACKGROUND OF THE INVENTION

1. Field of the Invention

This invention relates to a pharmaceutical composition containing saponin from medicinal ginseng, which is useful for the treatment and prevention of trouble which is due to glucocorticoids belonging to adrenocortical hormones.

2. Description of the Prior Art

It is well known that medicinal ginseng, particularly Panax ginseng C. A. Meyer belonging to the family Araliaceae and usually called Korean ginseng, has for a long time been used as a tonic, restorative, antiphlogistic, diuretic, or antidiabetic. Research has recently been under way to ascertain that its drug actions are due to the saponins which it contains.

It is known that glucocorticoids belonging to adrenocortical hormones, such as cortisone, provide an indispensable medicine which protects a living body from stress, and takes part in conversion of proteins to glucides, metabolism of lipids, or the like. They are frequently used by oral administration, injection, local insertion or in the form of an ointment for the treatment of allergic disorders such as Addison's disease, anterior pituitary insufficiency, serum disease and asthma bronchiale, inflammatory diseases such as conjunctivitis, keratitis and iritis, rheumatic fever, rheumatoid arthritis, diffuse collagen diseases such as periarteriitis nodosa and dermatomyositis, chronic lymphocytic leukemia, smallpox, nephrosis, or the like. They are, however, likely to cause side effects known as the Cushing's syndrome, including abnormal fat deposition and edema in the face, neck or body, such as moon face and buffalo neck, abnormal increase of appetite, increase of body weight, pigmentation of the skin and nails, skin keratinization, hyperglycemia, hypertension, muscle force reduction, hypokalemia, and worsening of the existing ulcer. They also cause serious trouble to the organs, such as atrophy of adrenal cortex.

As the result of their extensive research with saponins of medicinal ginseng, the inventors of this invention have discovered that the use of such saponin and glucocorticoids in combination is effective for preventing and curing serious trouble caused by glucocorticoids to the organs, and also has a synergistic effect on the treatment of burns or the like.

The saponins of medicinal ginsengs effectively act against the atrophy of the adrenal due to glucocorticoids and the accompanying reduction of plasma cortisol. They are useful for the treatment of the adrenal atrophy, and effective against the side effects associated therewith. The mechanism of their action against burns has not yet been clarified, but their use in combination with glucocorticoids has shown a clear synergistic effect which has not been achieved by glucocorticoids alone.

Although research is under way on the saponins of medicinal ginseng as mentioned before, it is believed to be an unexpected discovery that the saponins are effective against the adrenal atrophy.

SUMMARY OF THE INVENTION

According to this invention, there is provided a pharmaceutical composition comprising a glucocorticoid and a saponin from medicinal ginseng, which acts against the side effects of glucocorticoids, and a medicine for glucocorticoids containing a saponin of medicinal ginseng, which is useful for the prevention and treatment of adrenal atrophy, and any other trouble in the organs.

DESCRIPTION OF THE PREFERRED EMBODIMENTS

Panax ginseng C. A. Meyer is the most preferred ginseng containing saponin for the purposes of this invention. Other ginsengs of the same family may, however, be used. They include Panax japonicus C. A. Meyer, Panax quinquefolium LINNE, Panax pseudoginseng WALICH, and Panax notoginseng BURKILL.

For the purpose of this invention, it is possible to obtain saponin by preparing a crude drug from any of the aforementioned ginsengs, extracting the saponin from it, and refining it, or by the tissue culture of a piece of rhizome cut from ginseng, followed by the extraction and purification of the saponin therefrom. The word "saponin" as herein used means a mixture obtained by any such method, and consisting substantially of saponins.

The saponin can, for example, be obtained from a crude drug of ginseng in the following way. The active constituent of ginseng is extracted with water, a lower aliphatic alcohol, or a lower aliphatic alcohol containing water, and concentrated by evaporation to form an extract of ginseng. The ginseng used for this purpose may be defatted with an ordinary fat-soluble organic solvent, if required. The extract is dissolved in n-butanol, and water is added into the solution with a shake. After the solution is left stationary to separate the insoluble matter, the n-butanol layer is dried by evaporation. The residue is dissolved in a lower aliphatic alcohol, and the solution is injected into ether with stirring. The precipitate thereby formed is collected by filtration. See Japanese Patent Publication No. 5016/1973.

The extract thus obtained consists substantially of saponin, and can directly be used as an active constituent for the composition according to this invention.

For the purpose of this invention, the saponin contains the compounds of formulas (I), (II), and (III), which will hereinafter be described in detail, though the kind and quantity of its components may somewhat differ with the kind of the ginseng employed and its age of cultivation. Generally, the saponin is a yellow white or brown, bitter powder which is easily soluble in water, methanol and dilute methanol, soluble in ethanol, and insoluble in chloroform, ether and carbon tetrachloride. The acid hydrolysis of the saponin yields anhydrous dextrose from its water soluble portion, and panaxadiol ($C_{30}H_{52}O_3$) having a melting point of 205° C. and/or panaxatriol ($C_{30}H_{52}O_4$) having a melting point of 238° C. to 239° C. from its water insoluble portion.

The saponin may also be obtained by tissue culture, for example, in the following way. A tissue slice of ginseng rhizome is placed in a culture medium composed of 500 ml of the Knop liquid medium containing 1,000 mg of calcium sulfate, 250 mg of potassium nitrate, 250 mg of magnesium sulfate and 250 mg of potassium phosphate, per liter, 1 ml/lit. of d'Heller's mineral solution, 5% of anhydrous dextrose, $10^{-6}$ g of vitamin B, $10^{-6}$ g of biotin, $10^{-6}$ g of kinetin and 1% of agar, and is maintained at 26° C. for culture and growth, whereby a ginseng callus is obtained. The callus is increased in the same culture medium, and the saponin is extracted and purified as described before.

For the purpose of this invention, the saponin contains at least one of the ginsenosides represented by formulas (I) and (II) below, and may also in some cases contain β-D-glucopyranosyloleanate-(3)-β-D-glucopyranosyl(1→2)-β-D-glucuronopyranosido represented by formula (III).

Formula I is represented by the following:

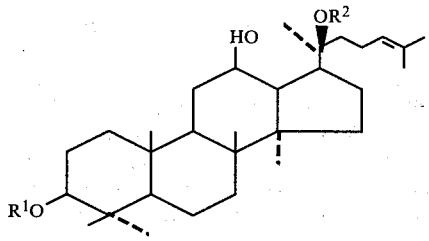

wherein $R^1$ represents a β-D-glucopyranosyl(1→2)-β-D-glucopyranosyl group, and $R^2$ represents a β-D-glucopyranosyl(1→6)-β-D-glucopyranosyl, α-L-arabinopyranosyl(1→6)-β-D-glucopyranosyl, β-D-xylopyranosyl(1→6)-β-D-glucopyranosyl, α-L-arabinofuranosyl(1→6)-β-D-glucopyranosyl or β-D-glucopyranosyl group.

Formula II is represented by the following:

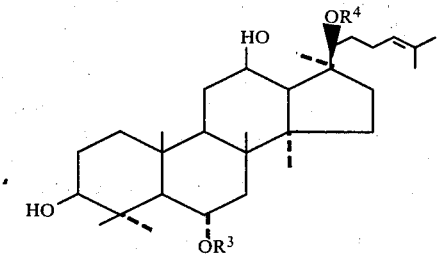

wherein $R^3$ represents an α-L-rhamnopyranosyl(1→2)-β-D-glucopyranosyl, β-D-glucopyranosyl(1→2)-β-D-glucopyranosyl, β-D-glucopyranosyl or α-L-rhamnopyranosyl(1→2)-β-D-glucopyranosyl group, and $R^4$ represents a hydrogen atom or a β-D-glucopyranosyl group.

Formula III is represented by the following:

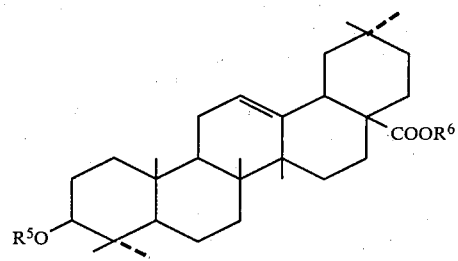

wherein $R^5$ represents a β-D-glucopyranosyl group, and $R^6$ represents a β-D-glucopyranosyl(1→2)-β-D-glucuronopyranosyl group.

The saponin represented by formula (I) or (II) is a saponin belonging to the dammarane glycosides of triterpenes. The saponins of formulas (I) and (II) are presently found solely in medicinal ginseng.

Specific examples of the compounds represented by formula (I) include 20S-protopanaxadiol-3-[O-β-D-glucopyranosyl(1→2)-β-D-glucopyranosido]-20-[O-β-D-glucopyranosyl(1→6)-β-D-glucopyranosido] (ginsenoside $Rb_1$), 20S-protopanaxadiol-3-[O-β-D-glucopyranosyl(1→2)-β-D-glucopyanosido]-20-[O-β-L-arabinopyranosyl(1→6)-β-D-glucopyranosido] (ginsenoside $Rb_2$), 20S-protopanaxadiol-3-[O-β-D-glucopyranosyl(1→2)-β-D-glucopyranosido]-20-[O-β-L-arabinofuranosyl(1→6)-β-D-glucopyranosido] (ginsenoside Rc), 20S-protopanaxadiol-3-[O-β-D-glucopyranosyl(1→2)-β-D-glucopyranosido]-20-[O-β-D-xylopyranosyl(1→6)-β-D-glucopyranosido] (ginsenoside $Rb_3$) and 20S-protopanaxadiol-3-[O-β-D-glucopyranosyl(1→2)-β-D-glucopyranosido]-20-[O-β-D-glucopyranosido] (ginsenoside Rd).

Specific examples of the compounds represented by formula (II) include 20-8-protopanaxatriol-6-[O-β-L-rhamnopyranosyl(1→2)-β-D-glucopyranosido]-20-O-β-D-glucopyranosido (ginsenoside Re), 20S-protopanaxatriol-6-O-β-D-glucopyranosyl(1→2)-β-D-glucopyranosido (ginsenoside Rf), 20S-protopanaxatriol-6-,20-di-O-β-D-glucopyranosido (ginsenoside $Rg_1$), 20S-protopanaxatriol-6-O-α-L-rhamnopyranosyl(1→2)-β-D-glucopyranosido (ginsenoside $Rg_2$), 20S-protopanaxatriol-6-[O-β-D-glucopyranosyl(1→2)-β-D-glucopyranosido]-20-O-β-D-glucopyranosido (ginsenoside 20-gluco-Rf), 20S-protopanaxatriol-6-O-β-D-glucopyranosido (ginsenoside $Rh_1$), and 20S-protopanaxatriol-20-O-β-D-glucopyranosido (ginsenoside $Rh_2$).

In addition to the saponins represented by formulas (I), (II) and (III), *Panax ginseng* C. A. MEYER contains a saponin having an unknown structure, but considered to have a skeleton similar to that of formula (I). It is called ginsenoside Ra, and belongs to the saponins for the purpose of this invention. See Chem. Pharm. Bull., 22(2), pages 421–428 (1974), and the Journal of Pharmacy, 94(2), pages 252–260 (1974).

The aforementioned individual compounds can be obtained if the saponin obtained as hereinbefore described is divided and purified, for example, by silica gel column chromatography or high speed liquid chromatography with a developing solvent composed of chloroform, methanol and water, or n-butanol, acetic acid and water. It is, however, economically advisable to use a mixture of the compounds, rather than dividing it into the individual saponins.

Glucocorticoids belong to the adrenocortical hormones, and specifically include cortisone, hydrocortisone, corticosterone, prednisone prednisolone, methyl prednisolone, triamcinolone, dexamethasone, paramethasone and betamethasone, and their acetate, succinate, phosphate and sulfate, and alkali metal salts of said succinate, phosphate and sulfate.

The dosage of the saponin according to this invention depends on the condition of a disease, but is generally 5 to 500 mg, preferably 10 to 250 mg, in three or four doses a day for internal use on an adult.

The dosage of the glucocorticoid depends on the kind of the compound used, and the condition of a disease. Acetate cortisone, which is a typical example of the glucocorticoids, is dosed in the amount of 5 to 30 mg a day, though as much as 200 to 400 mg a day may be used for the initial treatment of an actute disease.

It is desirable to use a single dosage form if the saponin and the glucocorticoid are used together.

Any known dosage form may be employed for the glucocorticoids, whether it may be for oral or parenteral administration. Examples of the dosage form for oral administration include tablets, powders, stock powders, granules, suspensions and lemonades. Examples of the dosage form for parenteral administration include injections, ointments, emulsions, pastes, poultices, and aerosols.

A preparation for oral administration should preferably contain 5 to 100 mg of saponin and 0.5 to 10 mg of glucocorticoid per gram or tablet. A parenteral preparation for external use should preferably contain 0.1 to 10% (w/v) of saponin and 0.05 to 1% (w/v) of glucocorticoid. An injection should preferably contain 5 to 50 mg of saponin and 1 to 25 mg of glucocorticoid per milliliter.

If the saponin alone is used, its dosage form may be chosen from among powders, tablets, injections, ointments, or the like. It can be formed into any such form of preparation.

These preparations may be produced by any method well known in the art, using excipients and various kinds of additives appropriately selected from among those known in the art.

The toxicity of the saponin is so low that it has shown a $LD_{50}$ of 637 mg/kg when administered intraperitoneally into mice. Therefore, an adequate daily dosage of saponin does not produce any side effect on a human body.

Attention is now directed to an example of the preparation of saponin from ginseng.

Ten (10) kg of rhizome slices of *Panax ginseng* C. A. Meyer (quadrennial) were heated for extraction three times each in 100 liters of methanol for three hours each, and the extracted solutions were put together and concentrated to 10 liters. The concentrate was gradually injected into 100 liters of ether under stirring, and the precipitate was dried until it did not have any odor of ether any longer. The dry product was dissolved in 10 liters of n-butanol saturated with water over a bath of vapor three times for about one hour each under stirring. The solution thus obtained was washed three times with 3 liters of n-butanol saturated water, so that the saccharides and pigments were removed by migration into the water. The water saturated n-butanol layer was separated, and dried by vacuum distillation at a temperature not higher than 80° C. The residue obtained was dissolved in 3 liters of methanol, and the solution was injected into 60 liters of ether under stirring. After the solution was left for one day as it was, the precipitate formed was collected by filtration, and dried under reduced pressure at a temperature not higher than 60° C., whereby 260 g of saponin were obtained. 100 g of this saponin was subjected to silica gel column chromatography with a developing agent composed of n-butanol, acetic acid and water, whereby ginsenosides $Rb_1$ and $Rg_1$ were isolated.

Description will now be made of examples of pharmacological tests and clinical treatment performed by using the saponin, the ginsenosides $Rb_1$ and $Rg_1$ obtained as hereinabove described.

PHARMACOLOGICAL TESTS

The saponins were tested for their effects on the adrenal atrophy and the blood plasma cortisole, as follows:

A. 5 mg/kg of dexamethasone were intraperitoneally administered every day for 10 days into male rats in groups of 10 each, having a weight of 130±2 g. The administration of the saponins was started on the 11th day. 10 mg/kg of ginseng saponin, 2 mg/kg of ginsenoside $Rb_1$ and 2 mg/kg of ginsenoside $Rg_1$ were intraperitoneally administered every day for 10 days into the rats of the respective groups. For a control group of rats, 1 ml/kg of a physiological saline solution was intraperitoneally administered for 10 days beginning on the 11th day. Then, the rats were abdominally cut, and the adrenal weight and the amount of the plasma cortisone were measured for each group of rats. The results were as follows:

|  | Blank | Physiological saline soln. | Saponin | $Rb_1$ | $Rg_1$ |
|---|---|---|---|---|---|
| Adrenal weight (mg) | 87 ± 6 | 28 ± 6 | 73 ± 6 | 49 ± 3 | 66 ± 4 |
| Plasma cortisol (μg/dl) | 73 ± 2 | 31 ± 8 | 61 ± 3 | 54 ± 2 | 59 ± 4 |

B. Likewise, 10 mg/kg of saponin, 2 mg/kg of ginsenoside $Rb_1$ and 2 mg/kg of ginsenoside $Rg_1$ were administered for three groups of ten rats each, respectively, as well as 1 ml/kg of a physiological saline solution for a control group of rats, for ten days continuously. Then, 5 mg/kg of dexamethasone were intraperitoneally administered for each group of rats for ten days continuously, beginning on the 11th day. The rats were abdominally cut, and their adrenal weight and the amount of plasma cortisol were measured. The following results were obtained:

|  | Blank | Physiological saline soln. | Saponin | $Rb_1$ | $Rg_1$ |
|---|---|---|---|---|---|
| Adrenal weight (mg) | 92 ± 3 | 25 ± 5 | 74 ± 4 | 53 ± 3 | 61 ± 4 |
| Plasma cortisol (μg/dl) | 70 ± 2 | 28 ± 4 | 58 ± 4 | 43 ± 4 | 50 ± 3 |

As is obvious from the test results set forth at A and B above, the saponin and its constituents, ginsenosides $Rb_1$ and $Rg_1$, are all markedly effective against the reduction in the weight due to the adrenal atrophy, and in the amount of plasma control. As described at B, they were also effective when administered prior to the glucocorticoid. Thus, the saponin and its constituents are useful for both treatment and prevention of diseases.

EXAMPLES OF CLINICAL TREATMENT

Case 1

A 59-year-old woman, whose case was diagnosed as chronic nephritis five years ago, started to take predonisolone two years ago, and had a buffalo neck during the fourth month thereafter. Accordingly, she started to take a powder containing 5 mg of prednisolone and 100 mg of saponin twice a day in the morning and the evening. Then, her buffalo neck was gradually improved, and after three months, her neck became distinguishable from the upper parts of her shoulders. She continued to take the powder for another three months, and her edema, languor, or the like disappeared.

Case 2

A 63-year-old woman, who had been taking 20 mg of prednisolone every day after her case was diagnosed as chronic rheumatic knee arthritis, suffered from adrenal cortical insufficiency to the extent that the 17-OHCS and 17-KS in her urine were 1 mg/day and 5 mg/day, respectively. She stopped taking prednisolone, and took instead 4 g of a powder containing 50 mg of saponin per gram (i.e., 200 mg of saponin) every day for one month, 2 g each in the morning and the evening. Her adrenal cortical function was improved to the extent that the 17-OHCS and 17-KS in her urine were 10 μg/day and 10 mg/day, respectively. She also did not have any withdrawal symptom or rebound phenomenon.

Case 3

A 32-year-old man, whose case was diagnosed as chronic rheumatic arthritis, did not take any adrenocortical hormone. He took a powder containing 5 mg of prednisolone and 10 mg of saponin every day in the morning and the evening. After four months, the serious pain, edema and motor disturbance on his knee joints were completely improved without any side effect of steroid.

Case 4

A 50-year-old woman got a blister with hot water in an area of 20 cm² on the back of her left hand. It was broken in an area of 4 cm², where her hand was inflamed, and a secreting fluid oozed out. She took a tablet containing 50 mg of saponin and 5 mg of prednisolone twice a day, and applied an ointment containing 1% (w/v) of saponin and 0.5% (w/v) of prednisolone to the affected part. After two days, the secreting fluid disappeared, and the affected part dried up. It was cured after five days without any pigmental disorder or scar formation. No side effect of steroid was observed. The treatment produced its effects surprisingly faster than in the usual cases where steroid alone was used.

What is claimed is:

1. A pharmaceutical composition comprising a saponin of medicinal ginseng and a glucocorticoid.

2. The pharmaceutical composition of claim 1, wherein said saponin is obtained from *Panax ginseng* C. A. Mayer, *Panax quinquefolium* Linne, *Panax pseudoginseng* WALICH or *Panax notoginseng* BURKILL.

3. The pharmaceutical composition of claim 1, wherein said saponin is obtained from *Panax ginseng* C. A. Meyer.

4. The pharmaceutical composition of claim 1, wherein said saponin contains a compound of formula I:

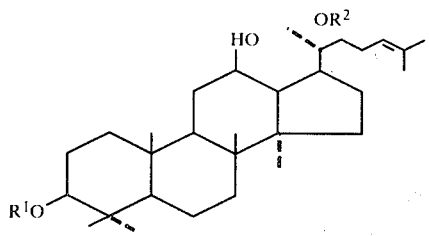

wherein $R^1$ represents a β-D-glucopyranosyl(1→2)-β-D-glucopyranosyl group, and R represents a β-D-glucopyranosyl(1→6)-β-D-glucopyranosyl,α-L-arabinopyranosyl(1→6)-β-D-glucopyranosyl,β-D-xylopyranosyl(1→6)-β-D-glucopyranosyl,α-L-arabinofuranosyl(1→6)-β-D-glucopyranosyl or β-D-glucopyranosyl group.

5. The pharmaceutical composition of claim 1, wherein said saponin contains a compound of formula II:

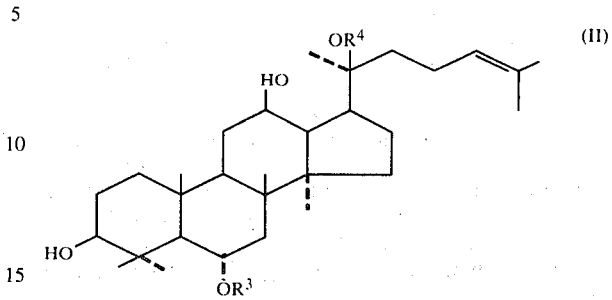

wherein $R^3$ represents an α-L-rhamnopyranosyl(1→2)-β-D-glucopyranosyl,β-D-glucopyranosyl(1→2)-β-D-glucopyranosyl,β-D-glucopyranosyl or α-L-rhamnopyranosyl(1→2)-β-D-glucopyranosyl group, and $R^4$ represents a hydrogen atom or a β-D-glucopyranosyl group.

6. The pharmaceutical composition of claim 1, wherein said saponin contains a compound of formula I:

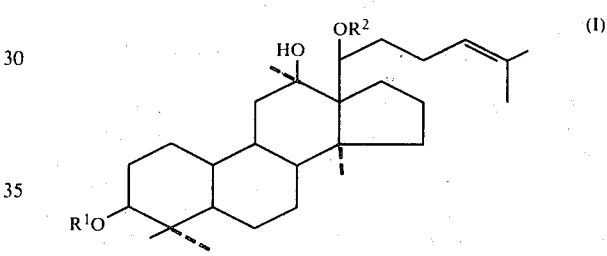

wherein $R^1$ represents a β-D-glucopyranosyl(1→2)-β-D-glucopyranosyl group, and $R^2$ represents a β-D-glucopyranosyl(1→6)-β-D-glucopyranosyl,α-L-arabinopyranosyl(1→6)-β-D-glucopyranosyl,β-D-xylopyranosyl(1→6)-β-D-glucopyranosyl,α-L-arabinofuranosyl(1→6)-β-D-glucopyranosyl or β-D-glucopyranosyl group, and a compound of formula II:

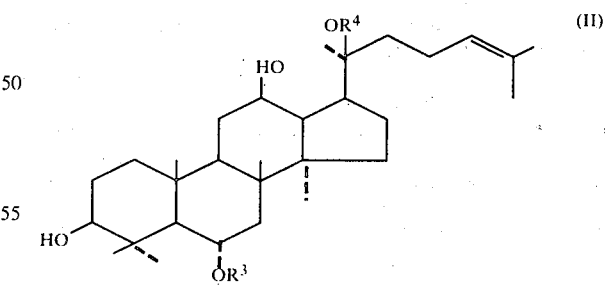

wherein $R^3$ represents an α-L-rhamnopyranosyl(1→2)-β-D-glucopyranosyl,β-D-glucopyranosyl(1→2)-β-D-glucopyranosyl,β-D-glucopyranosyl or α-L-rhamnopyranosyl(1→2)-β-D-glucopyranosyl group, and $R^4$ represents a hydrogen atom or a β-D-glucopyranosyl group.

7. The pharmaceutical composition of any of claims 4-6, wherein said saponin contains a compound of formula III:

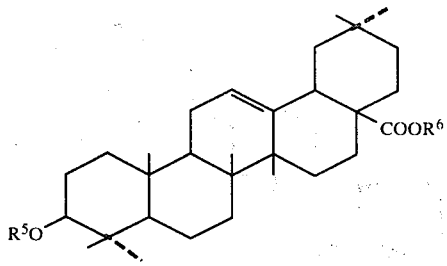

wherein R⁵ represents a β-D-glucopyranosyl group, and R⁶ represents a β-D-glucopyranosyl(1→2)-β-D-glucuronopyranosyl group.

8. A pharmaceutical composition comprising a glucocorticoid and a saponin selected from the group consisting of compounds of the formulae I, II, and III which are defined in claims 4, 5 and 7, respectively.

9. The pharmaceutical composition according to claim 1, wherein said glucocorticoid is selected from the group consisting of cortisone, hydrocortisone, corticosterone, prednisone, prednisolone, methyl prednisolone, triamcinolone, dexamethasone, paramethasone and betamethasone; their acetate, succinate, phosphate and sulfate; and alkali metal salts of said succinate, phosphate and sulfate.

10. The pharmaceutical composition according to claim 1, which is in the form of an external preparation wherein 0.1 to 10% (w/v) of said saponin and 0.05 to 1% (w/v) of said glucocorticoid are contained.

11. The pharmaceutical composition according to claim 1, which is in the form of an oral preparation wherein 5 to 100 mg of said saponin and 0.5 to 10 mg of said glucocorticoid are contained per one gram or one tablet.

12. The pharmaceutical composition according to claim 1, which is in the form for an injection administration wherein 5 to 50 mg of said saponin and 1 to 25 mg of said glucocorticoid are contained per ml.

13. A method of preventing adrenal atrophy comprising administering to a host a therapeutically effective amount of the composition according to claim 1.

14. A method of treating adrenal atrophy comprising administering to a patient afflicted with adrenal atrophy a therapeutically effective amount of the composition according to claim 1.

15. A method of preventing adrenal atrophy comprising administering to a patient a therapeutically effective amount of a saponin of medicinal ginseng.

16. A method of treating adrenal atrophy comprising administering to a patient afflicted with adrenal atrophy a therapeutically effective amount of a saponin of medicinal ginseng.

17. The method according to any of claims 13, 14, 15 or 16, wherein said orally therapeutically effective amount of said saponin is 5 to 500 mg in three or four doses a day.

18. A method of treating adrenal atrophy comprising administering to a patient afflicted with adrenal atrophy a glucocorticoid and thereafter administering a saponin of medicinal ginseng.

19. A method of treating adrenal atrophy comprising administering to a patient afflicted with adrenal atrophy a therapeutically effective amount of 20S-protopanaxadiol-3-[O-β-D-glucopyranosyl(1→2)-β-D-glucopyranosido]-20-[O-β-D-glucopyranosyl(1→6)-β-D-glucopyranosido] (ginsenoside Rb₁).

20. A method of treating adrenal atrophy comprising administering to a patient afflicted with adrenal atrophy a therapeutically effective amount of 20 S-protopanaxatriol-6-,20-di-O-β-D-glucopyranosido (ginsenoside Rg₁).

21. A method of treating skin burns comprising administering to a patient suffering from a skin burn a therapeutically effective amount of the composition according to claim 1.

22. A method of preventing adrenal atrophy comprising administering to a host a therapeutically effective amount of a composition comprising a saponin of medicinal ginseng and prednisolone.

23. A method of treating adrenal atrophy comprising administering to a patient afflicted with adrenal atrophy a therapeutically effective amount of a composition comprising a saponin of medicinal ginseng and prednisolone.

24. A method of preventing adrenal atrophy comprising administering to a host a therapeutically effective amount of a composition comprising a saponin of medicinal ginseng and a glucocorticoid selected from the group consisting of cortisone acetate, dexamethasone, hydrocortisone, paramethasone and triamcinolone.

25. A method of treating adrenal atrophy comprising administering to a patient afflicted with adrenal atrophy a therapeutically effective amount of a composition comprising a saponin of medicinal ginseng and a glucocorticoid selected from the group consisting of cortisone acetate, dexamethasone, hydrocortisone, paramethasone and triamcinolone.

26. A method according to claim 15, wherein said saponin contains a compound selected from the group consisting of a compound of formula I:

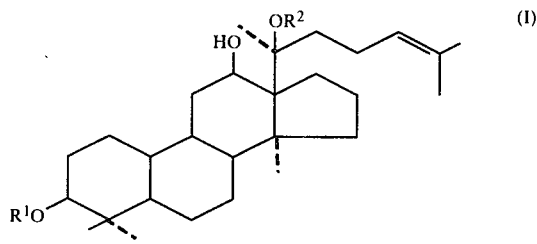

wherein R¹ represents a β-D-glucopyranosyl(1→2)-β-D-glucopyranosyl group, and R² represents a β-D-glucopyranosyl(1→6)-β-D-glucopyranosyl,β-L-arabinopyranosyl(1→6)-β-D-glucopyranosyl,β-D-xylopyranosyl(1→6)-β-D-glucopyranosyl,α-L-arabinofuranosyl(1→6)-β-D-glucopyranosyl or β-D-glucopyranosyl group, a compound of formula II:

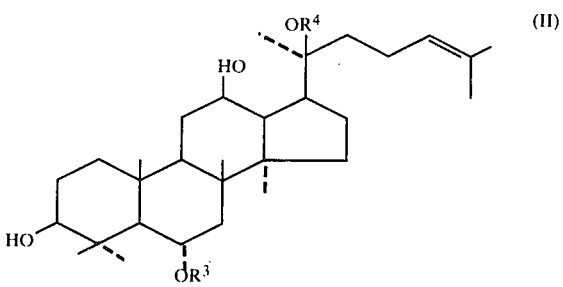

wherein R³ represents an α-L-rhamnopyranosyl(1→2)-β-D-glucopyranosyl,β-D-glucopyranosyl(1→2)-β-D- glucopyranosyl,β-D-glucopyranosyl or α-L-rhamnopyranosyl(1→2)-β-D-glucopyranosyl group, and R⁴ represents a hydrogen atom or a β-D-glucopyranosyl group, a compound of formula III:
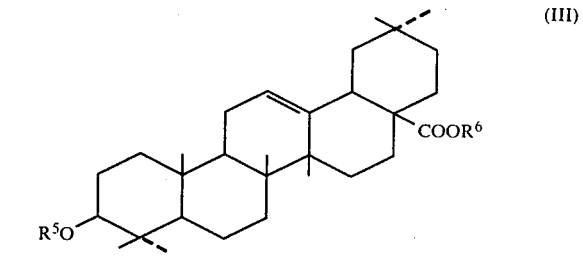
wherein $R^5$ represents a β-D-glucopyranosyl group, and $R^6$ represents a β-D-glucopyranosyl(1→2)-β-D-glucuronopyranosyl group, and mixtures thereof.
* * * * *